(12) United States Patent
Shokoohi

(10) Patent No.: US 8,303,650 B2
(45) Date of Patent: Nov. 6, 2012

(54) BIODEGRADABLE SELF-EXPANDING DRUG-ELUTING PROSTHESIS

(75) Inventor: Mehrdad M. Shokoohi, Miami, FL (US)

(73) Assignee: Telesis Research, LLC, Coral Gables, FL (US)

( * ) Notice: Subject to any disclaimer, the term of this patent is extended or adjusted under 35 U.S.C. 154(b) by 655 days.

(21) Appl. No.: 11/972,406

(22) Filed: Jan. 10, 2008

(65) Prior Publication Data

US 2009/0182404 A1  Jul. 16, 2009

(51) Int. Cl.
*A61F 2/06* (2006.01)

(52) U.S. Cl. ............... 623/1.42; 623/1.11; 623/1.34; 623/1.35; 623/1.46

(58) Field of Classification Search ............... 623/1.15, 623/1.42–1.46, 1.49–1.51, 1.53
See application file for complete search history.

(56) References Cited

U.S. PATENT DOCUMENTS

| | | | |
|---|---|---|---|
| 4,655,771 A | 4/1987 | Wallsten | |
| 4,954,126 A | 9/1990 | Wallsten | |
| 5,026,377 A | 6/1991 | Burton et al. | |
| 5,061,275 A | 10/1991 | Wallsten et al. | |
| 5,176,907 A | 1/1993 | Leong | |
| 5,194,581 A | 3/1993 | Leong | |
| 5,256,765 A | 10/1993 | Leong | |
| 5,527,337 A | 6/1996 | Stack et al. | |
| 5,545,208 A | 8/1996 | Wolff et al. | |
| 5,551,954 A | 9/1996 | Buscemi et al. | |
| 5,630,840 A | 5/1997 | Mayer | |
| 5,645,559 A | 7/1997 | Hachtman et al. | |
| 5,667,523 A | 9/1997 | Bynon et al. | |
| 5,700,901 A | 12/1997 | Hurst et al. | |
| 5,718,159 A | 2/1998 | Thompson | |
| 5,741,333 A | 4/1998 | Frid | |
| 5,755,772 A * | 5/1998 | Evans et al. | 128/898 |
| 5,853,419 A * | 12/1998 | Imran | 623/1.15 |
| 5,997,468 A | 12/1999 | Wolff et al. | |
| 6,042,578 A | 3/2000 | Dinh et al. | |
| 6,156,064 A * | 12/2000 | Chouinard | 623/1.44 |
| 6,245,103 B1 | 6/2001 | Stinson | |
| 6,295,714 B1 | 10/2001 | Roychowdhury et al. | |
| 6,551,352 B2 | 4/2003 | Clerc et al. | |
| 6,626,939 B1 | 9/2003 | Burnside et al. | |
| 6,652,582 B1 | 11/2003 | Stinson | |
| 6,719,934 B2 | 4/2004 | Stinson | |
| 6,991,647 B2 | 1/2006 | Jadhav | |
| 6,997,948 B2 | 2/2006 | Stinson | |
| 7,001,425 B2 | 2/2006 | McCullagh et al. | |
| 7,163,555 B2 | 1/2007 | Dinh | |

(Continued)

OTHER PUBLICATIONS

Leach et al., *Degradation of double-walled microspheres of PLLA and P(CPP:SA) 20:80. I. In vitro degradation*, Biomaterials 19 (1998) pp. 1973-1980.

Xu et al., *Polyphosphoester microspheres for sustaining release of biologically active nerve growth factor*, Biomaterials 23 (2002) pp. 3765-3772.

(Continued)

*Primary Examiner* — Thomas J Sweet
*Assistant Examiner* — Yashita Sharma
(74) *Attorney, Agent, or Firm* — Knobbe, Martens, Olson & Bear LLP

(57) ABSTRACT

Disclosed herein is a biodegradable prosthesis that includes a first end, a second end, and an elongate tubular body with a lumen therethrough. The prosthesis has a first outer layer with a drug delivery element that may include polyphosphoester microspheres. The prosthesis also can have a second layer comprising a set of flexible interbraided bioabsorbable filaments. Also, the prosthesis can have a third inner layer comprising a porous thermoplastic material.

20 Claims, 17 Drawing Sheets

U.S. PATENT DOCUMENTS

| | | | |
|---|---|---|---|
| 7,226,473 B2 * | 6/2007 | Brar et al. ............... | 623/1.11 |
| 2001/0056299 A1 | 12/2001 | Thompson | |
| 2002/0147492 A1 | 10/2002 | Shokoohi et al. | |
| 2004/0162606 A1 | 8/2004 | Thompson | |
| 2004/0167606 A1 | 8/2004 | Chouinard | |
| 2004/0193241 A1 | 9/2004 | Stinson | |
| 2005/0209676 A1 | 9/2005 | Kusleika | |
| 2005/0283224 A1 * | 12/2005 | King ............... | 623/1.13 |
| 2006/0052859 A1 | 3/2006 | Igaki | |
| 2006/0057183 A1 | 3/2006 | Nakano et al. | |
| 2006/0058867 A1 | 3/2006 | Thistle et al. | |
| 2006/0070516 A1 | 4/2006 | McCullagh et al. | |
| 2006/0129222 A1 | 6/2006 | Stinson | |
| 2006/0195175 A1 * | 8/2006 | Bregulla ............... | 623/1.15 |
| 2006/0224234 A1 | 10/2006 | Jayaraman | |
| 2006/0266474 A1 | 11/2006 | Burnside et al. | |
| 2007/0100437 A1 * | 5/2007 | Welborn et al. ............... | 623/1.44 |
| 2007/0123977 A1 * | 5/2007 | Cottone et al. ............... | 623/1.42 |
| 2007/0255394 A1 | 11/2007 | Ryan | |
| 2010/0016940 A1 | 1/2010 | Shokoohi et al. | |

OTHER PUBLICATIONS

Shi et al., *Double walled POE/PLGA microspheres: encapsulation of water-soluble and water-insoluble proteins and their release properties*, Journal of Controlled Release 89 (2003) pp. 167-177.

Yang et al., *POE/PLGA composite microspheres: formation and in vitro behavior of double walled microspheres*, Journal of Controlled Release 88 (2003) pp. 201-213.

Berkland et al., *Uniform double-walled polymer microspheres of controllable shell thickness*, Journal of Controlled Release 96 (2004) pp. 101-111.

Pollauf et al., *Use of thermodynamic parameters for design of double-walled microsphere fabrication methods*, Biomaterials 27 (2006) pp. 2898-2906.

Mao, et al., "Biodegradable poly(terephthalate-co-phosphate)s: synthesis, characterization and drug-release properties", J. Biomater Sci Polym Ed. 2005; 16(2): pp. 135-161.

International Search Report for PCT/US09/30485 mailed Mar. 3, 2009.

International Search Report dated Sep. 14, 2010 PCT/US2010/042013 in 12 pages.

* cited by examiner

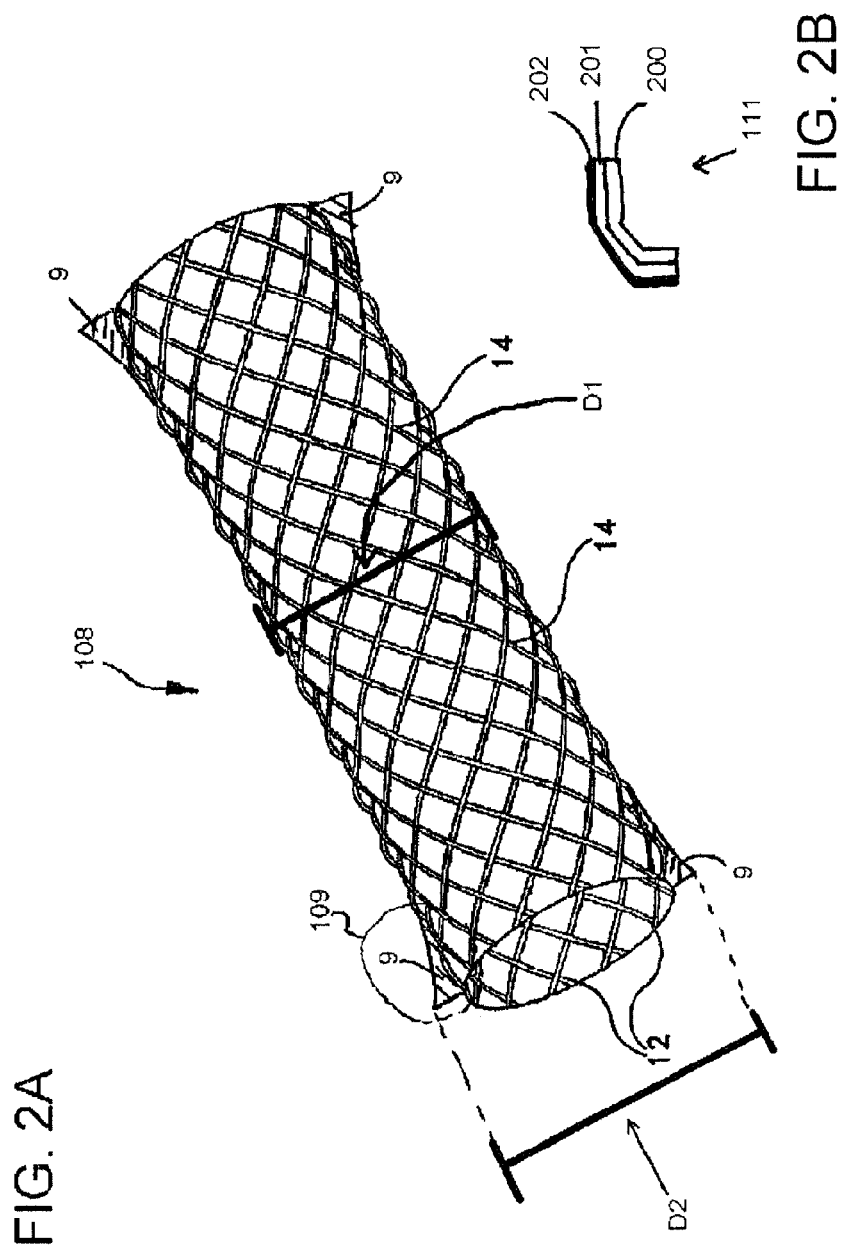

FIG. 4
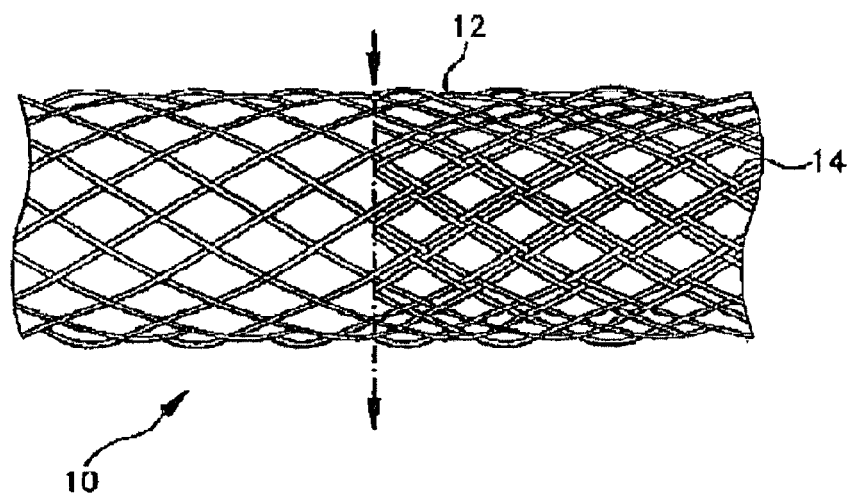
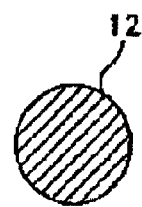
FIG. 5

BIODEGRADABLE SELF-EXPANDING DRUG-ELUTING PROSTHESIS

FIELD OF THE INVENTION

The present invention relates generally to implantable, radially expandable medical prostheses, often referred to as stents.

DESCRIPTION OF THE RELATED ART

The present invention relates generally to implantable, radially expandable medical prostheses which are frequently referred to as stents. In particular, some embodiments of the invention include a bioabsorbable self-expanding stent with a controlled-release drug layer.

Atherosclerotic disease, for example, causes localized occlusion of the blood vessels resulting from the build-up of plaque. As the deposits increase in size, they reduce the diameter of the arteries and impede blood circulation.

Restenosis is the reclosure of a peripheral or coronary artery following trauma to that artery caused by efforts to open a stenosed portion of the artery, such as, for example, by balloon dilation, ablation, atherectomy or laser treatment of the artery. For these angioplasty procedures, restenosis occurs at a rate of about 20-50% depending on the definition, vessel location, lesion length and a number of other morphological and clinical variables. Restenosis is believed to be a natural healing reaction to the injury of the arterial wall that is caused by angioplasty procedures. The healing reaction begins with the thrombotic mechanism at the site of the injury. The final result of the complex steps of the healing process can be intimal hyperplasia, the uncontrolled migration and proliferation of medial smooth muscle cells, combined with their extracellular matrix production, until the artery is again stenosed or occluded.

Self-expanding medical prostheses frequently referred to as stents are well known and commercially available. They are; for example, disclosed generally in U.S. Pat. No. 4,655,771 to Wallsten, U.S. Pat. No. 5,061,275 to Wallsten et al., and Hachtmann et al., U.S. Pat. No. 5,645,559, which are all hereby incorporated by reference in their entirety. Devices are used within body vessels of humans for a variety of medical applications. Examples include intravascular stents for treating stenoses, stents for maintaining openings in the urinary, biliary, tracheobronchial, esophageal, and renal tracts, and vena cava filters.

A delivery device which retains the stent in its compressed state is used to deliver the stent to a treatment site through vessels in the body. The flexible nature and reduced radius of the compressed stent enables it to be delivered through relatively small and curved vessels. In percutaneous transluminal angioplasty, an implantable endoprosthesis is introduced through a small percutaneous puncture site, airway, or port and is passed through various body vessels to the treatment site. After the stent is positioned at the treatment site, the delivery device is actuated to release the stent, thereby allowing the stent to self-expand within the body vessel. The delivery device is then detached from the stent and removed from the patient. The stent remains in the vessel at the treatment site as an implant.

Stents must exhibit a relatively high degree of biocompatibility since they are implanted in the body. An endoprosthesis may be delivered into a body lumen on or within a surgical delivery system such as delivery devices shown in U.S. Pat. Nos. 4,954,126 and 5,026,377, which are hereby incorporated by reference in their entirety. Delivery devices that can be used for the present invention include U.S. Pat. Nos. 4,954,126 and 5,026,377, which are hereby incorporated by reference in their entirety. Suitable materials for use with such delivery devices are described in U.S. Pat. No. 6,042,578, hereby incorporated by reference in its entirety.

Commonly used materials for known stent filaments include Elgiloy® and Phynox® metal spring alloys. Other metallic materials than can be used for self-expanding stent filaments are 316 LVM stainless steel, MP35N alloy, and superelastic Nitinol nickel-titanium alloy including shape memory and temperature sensitive types. Another self-expanding stent, available from Schneider (USA) Inc. of Minneapolis, Minn., has a radiopaque clad composite structure such as shown in U.S. Pat. No. 5,630,840 to Mayer. Self-expanding stents can be made of a Titanium Alloy as described in U.S. Pat. No. 6,042,578, hereby incorporated by reference in its entirety.

The strength and modulus of elasticity of the filaments forming the stents are also important characteristics. Elgiloy®, Phynox®, MP35N and stainless steel are all high strength and high modulus metals. Nitinol has relatively low strength and modulus.

The implantation of an intraluminal stent will preferably cause a generally reduced amount of acute and chronic trauma to the luminal wall while performing its function. A stent that applies a gentle radial force against the wall and that is compliant and flexible with lumen movements is preferred for use in diseased, weakened, or brittle lumens. The stent will preferably be capable of withstanding radially occlusive pressure from tumors, plaque, and luminal recoil and remodeling.

Pharmacologic attempts have been made to reduce the rate of restenosis. These attempts have generally dealt with the systemic delivery of drugs via oral, intravascular, or intramuscular introduction. Little, if any success has been achieved with this systemic approach.

For drug delivery, it has been recognized for a long period of time that pills and injections may not be the best mode of administration. It is very difficult with these types of administration to obtain constant drug delivery. Patient noncompliance with instructions is also a problem. Through repeated doses, these drugs often cycle through concentration peaks and valleys, resulting in time periods of toxicity and ineffectiveness. Thus, localized drug treatment is warranted.

There remains a continuing need for self-expanding stents with particular characteristics for use in various medical indications. Stents are needed for implantation in an ever growing list of vessels in the body. Different physiological environments are encountered and it is recognized that there is no universally acceptable set of stent characteristics.

A need exists for a stent which has self expanding characteristics, but which is bioabsorbable, as well as a controlled-release drug delivery. A surgical implant such as a stent endoprosthesis must be made of a non-toxic, biocompatible material in order to minimize the foreign-body response of the host tissue. The implant must also have sufficient structural strength, biostability, size, and durability to withstand the conditions and confinement in a body lumen.

All documents cited herein, including the foregoing, are incorporated herein by reference in their entireties for all purposes.

SUMMARY OF THE INVENTION

There is provided in accordance with one aspect of the present invention, a hybrid biodegradable prosthesis. The prosthesis comprises a first end, a second end, and an elongate tubular body with a lumen therethrough. An outer layer comprises a drug delivery element. In one embodiment, the drug delivery element comprises polyphosphoester microspheres. The middle layer may comprise a plurality of flexible inter-braided bioabsorbable filaments. An inner layer comprises a porous thermoplastic material. The inner layer provides a conduit for blood flow, and is configured to integrate into the vascular tissue. Thus, the prosthesis is a hybrid device, in which a first portion is absorbable or erodable over time, and a second portion is incorporated by cellular in-growth into the vascular intima.

In accordance with another aspect of the present invention there is provided a method of treating a patient. The method comprises the steps of providing a coaxial delivery system, including a catheter, loaded with a stent as described above. The catheter is advanced to a treatment site and the stent is deployed at the treatment site.

In accordance with a further aspect of the present invention, there is provided a medical system. This system comprises a catheter, having a radially expandable hybrid stent loaded thereon having an absorbable component and a permanent component.

An outer diameter at the first end of the prosthesis can be larger than a smaller outer diameter at a mid-point on the prosthesis axially displaced from the first end of the prosthesis. The larger diameter may be at least about 0.005 inches or more, or between about 5-9% greater in some embodiments than the smaller diameter. The outer layer may include any drug or biologically active substance depending on the desired clinical result, such as paclitaxel, rapamycin, zotarolimus, or tacrolimus.

The middle layer can be annealed to the inner layer. The bioabsorbable filaments can comprise a material selected from the group consisting of polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester; poly(amino acids), and poly(alpha-hydroxy acid). In some embodiments, the first end and/or the second end of the prosthesis comprise a drug delivery reservoir. In some embodiments, at least the first end or the second end of the stent is flared and folded to provide enhanced radial support. The stent may include at least one radioopaque marker element. The prosthesis can further include a second drug delivery element on an inner surface of the inner layer of the stent.

Also disclosed herein is a method of forming a vascular prosthesis, comprising: the steps of providing a first tubular body comprising a porous thermoplastic material; providing a second tubular body comprising a plurality of bioabsorbable filaments woven helically along a central axis of the second tubular body, the second tubular body having a outer diameter greater than that of the first tubular body; annealing the first tubular body to the second tubular body; and applying a coating layer to an outer surface of the second tubular body. In some embodiments, a crossing angle of the helically woven bioabsorbable filaments is between about 120 and 160 degrees. In some embodiments, applying a coating layer involves one of spraying or dipping. The coating can be a drug coating.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 2A illustrates a stent with enlarged, flared, tapered proximal and distal ends, according to one embodiment of the invention.

FIG. 2B is a close-up side view of a cross-section of the stent ends shown of FIG. 2A that illustrates flared ends of the stent. The inner synthetic membrane layer may be compressed, laminated, and/or bonded to the braided bioabsorbable layer, such as through induction of heat and compression.

FIGS. 3-4 illustrates in intermediate stent layer with biodegradable interwound filaments, which can provide increased radial support for the stent, according to one embodiment of the invention.

FIG. 5 illustrates a cross-section of a polymeric filament.

DETAILED DESCRIPTION OF THE PREFERRED EMBODIMENT

The present invention relates generally to a hybrid construct adapted for implantation in a living organism, such as a human. The construct includes at least a first portion which is bioabsorbable, and may support a drug delivery characteristic. The bioabsorbable component may be attached to a non-absorbable or permanent component. Thus, following implantation in the body, the bioabsorbable component gradually disappears, while the permanent component becomes attached to and/or integrated within the adjacent tissue. The term 'bioabsorbable' is used herein only to indicate a transient presence in the body, and to include all mechanisms by which the implant or implant component may disappear over time, including dissolution, absorption, erosion or others.

The hybrid construct of the present invention will be described primarily herein in a tubular form, particularly adapted for implantation within the cardiovascular system. It should be appreciated that the tubular form of the present invention may also be configured for implantation within other hollow organs or tubular structures within the body, such as the gastro intestinal tract including the stomach, esophagus, various portions of the intestine and colon. The tubular construct may alternatively be configured for positioning in the airways, such as the trachea, bronchial tubes, or other portions of the lung, and the sinus and nasal cavities. Alternative embodiments may be configured for implantation within the urethra, ureters, fallopian tubes, uterus, vagina, or elsewhere as will be appreciated by those of skill in the art. Within the cardiovascular system, tubular embodiments of the present invention may be configured for implantation within the coronary vasculature, peripheral vasculature, and intracranial vasculature. Additional indications will be discussed below.

Nontubular embodiments of the present invention may be provided in the form of a multilayer patch, which may be utilized to span or repair any of a variety of tissue defects, such as hernias, ulcerations, perforations, or other defects or injuries caused by surgery, traumatic injury or disease states.

Figure 1:
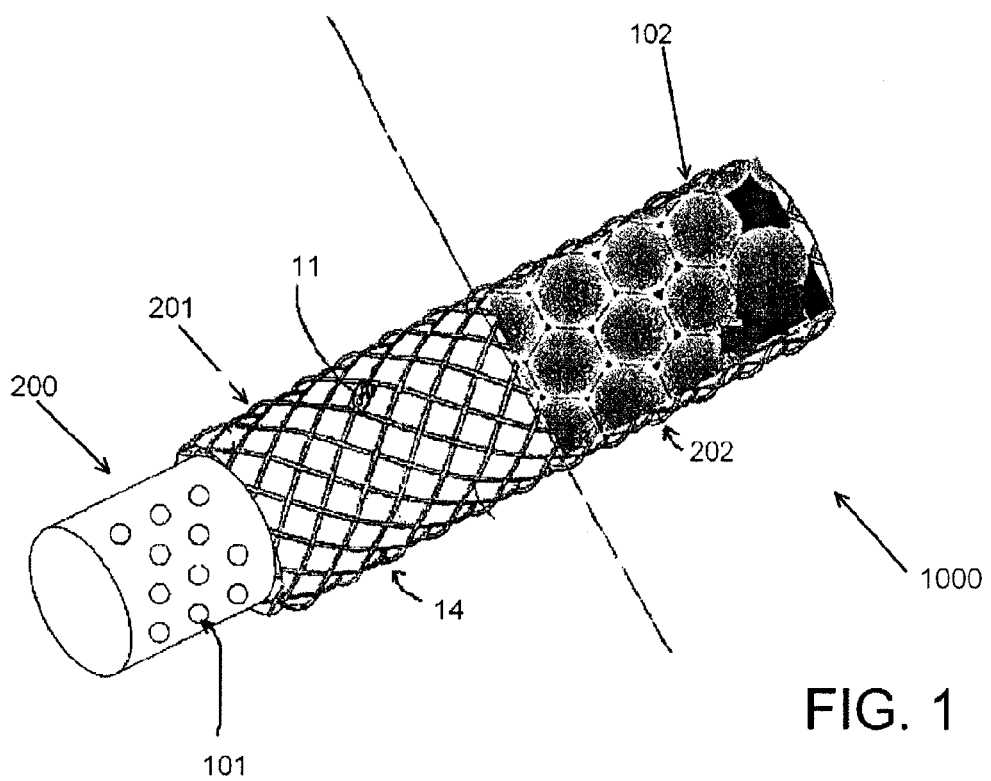
FIG. 1 schematically illustrates in partial cut away view various sections of a multilayer self-expanding prosthesis according to one embodiment of the invention.

For example, the embodiment illustrated in FIG. 1 comprises at least three layers formed in a tubular configuration for intravascular implantation. Although described below as discrete layers, it should be appreciated that the composition of each of the three layers may be interwoven or intermingled with the adjacent layer or layers as will be appreciated by those of skill in the art in view of the description herein.

Referring to FIG. 1, a structural intermediate support layer 201 may comprise a woven braided helically wound or otherwise configured fabric or filament structure. The filament layer 201 may be absorbable as is disclosed elsewhere herein. Preferably, the filament layer 201 is self-expandable from a reduced cross-sectional configuration such as for transluminal navigation to a deployment site, to an enlarged cross-sectional configuration such as for lining a vessel. The filament layer 201 is sometimes referred to herein as the second or intermediate layer.

Disposed concentrically within the central lumen defined by the second layer 201 is an inner first layer 200. The inner first layer 200 comprises a thin membrane discussed in greater detail below. In certain embodiments, the membrane is provided with a microporous or macroporous structure configured to permit cellular in-growth from the adjacent vascular wall, optimally of a nature sufficient to provide a viable neointimal lining on the inner, luminal surface of the implant.

The outermost or third layer 202 comprises a drug release characteristic. The drug release characteristic may be provided in any of a variety of ways, such as by inclusion of microspheres on the surface of the construct, dipping, spraying or other coating operations, chemical and/or mechanical binder layers or tie layers or the like. The outer layer 202 may thus reside within the interstitial spaces between the adjacent filaments of the second layer 201 and/or radially outwardly disposed with respect to the filaments of the second layer 201. Alternatively, the outer layer 202 may comprise a coating upon each individual filament, as is discussed below.

In general terms, the construct of the present invention is intended to be transvascularly advanced to a treatment site and deployed such that the outer layer 202 is brought into contact with the intimal lining of the vessel, through the self-expanding characteristic created by the second layer 201 and potentially assisted by the first layer 200. This permits blood flow through the central lumen, while the drug delivery layer is maintained against the vessel wall. The construct remains in position while drug is eluted from the outer layer 202. In an absorbable embodiment, at least a first portion of the stent which may include the second layer 201 and an outer layer 202 may be absorbable or erodable at the implantation site. At the same time, the intermediate tubular layer 200 may be non-erodable. In this embodiment, after a desired predetermined period of time, the implant ceases to deliver drug from the outer layer 202, the second layer 201 and outer layer 202 gradually are absorbed by the body, and cellular in-growth from the vessel wall enters the porous structure of the first layer 200, to provide a robust cellular lining on the luminal surface of the first layer 200. In this manner, the tubular layer 200 is integrated into the vessel wall and thus becomes biologically "invisible" to blood flow through the vessel.

FIG. 1 schematically illustrates in a partial cut-away view various sections of an embodiment of a self-expanding multilayer prosthesis 1000, or stent that is preferably at least partially bioresorbable in some embodiments. The prosthesis 1000 comprises multiple layers. A first layer 200 which is preferably the innermost layer, can be a membrane made of a biocompatible material such polyethylene, polyurethane, Teflon, or ePTFE with a thickness of about 0.001 to 0.010 inches, preferably between about 0.002 to 0.005 inches. The first layer 200 is preferably porous (e.g., via pores 101). Porous as used herein includes tortuous pathways such as is present in the fibril and node structure of ePTFE. The biocompatible membranous layer 200 can be, in some embodiments, interwound radially to a second layer 201 of bioabsorbable helically wound polymeric filaments 14, for example, polylactic acid-polyethylene oxide copolymers, polydioxanone, polyglycolic acid, polylactic acid, polycaprolactone, polycarolactone, polygluconate, polyanhyride, polyaminoacids, and combinations thereof, as discussed in greater detail below.

The outer layer 202 preferably comprises a controlled drug release element 102, which may be incorporated into polyphosphate ester microspheres deposited on layer 201 in some embodiments. In some embodiments, the controlled drug release element layer may be deposited on either or both of the inner and outer surfaces of the biocompatible layer 200 and/or the polymeric filament layer 201. The drug may be any drug known in the art. In some embodiments, the drug is an immunosuppressant or antiproliferative agent, such as paclitaxel (Taxol), rapamycin (Sirolimus), zotarolimus, or tacrolimus. In other embodiments, the drug may be an anti-platelet agent such as heparin, hirudin, or enoxaparin, or any other drug or bioactive compound depending on the desired clinical result.

Stent 1000 may also include one or more radioopaque marker elements 11 as discussed in greater detail below.

To satisfy the clinical needs on drug-eluting stents, in terms of providing the effective concentration of bioactive active agents in a timely manner, some embodiments provide one or more pharmaceutical agents which can be highly efficacious in controlling virtually all the biological events leading to restenosis.

In some embodiments, the prosthesis has a cambered interior surface of between about 10 to 20 degrees, similar to that disclosed in U.S. Pat. No. 5,551,954 to Buscemi et al, which is hereby incorporated by reference in its entirety.

Controlled release of a drug, via, for example, a bioabsorbable polymer offers to maintain the drug level within the desired therapeutic range for the duration of the treatment. In the case of stents, the prosthesis materials will maintain vessel support for weeks, months, or more or until incorporated into the vessel wall even with bioabsorbable, biodegradable polymer constructions. While the drug release layer is depicted as the outermost layer, it can be alternatively present as an inner or intermediate layer. In some embodiments, multiple drug release layers may be present.

Several polymeric compounds that are known to be bioabsorbable and hypothetically have the ability to be drug impregnated may be useful in prosthesis formation herein. These compounds include: poly-1-lactic acid/polyglycolic acid, polyanhydride, and polyphosphate ester. A brief description of each is given below.

Poly-1-lactic acid/polyglycolic acid has been used for many years in the area of bioabsorbable sutures. It is currently available in many forms, i.e., crystals, fibers, blocks, plates, etc. These compounds degrade into non-toxic lactic and glycolic acids.

Another compound which could be used are the polyanhydrides. They are currently being used with several chemotherapy drugs for the treatment of cancerous tumors. These drugs are compounded into the polymer which is molded into a cube-like structure and surgically implanted at the tumor site.

In some embodiments, the drug delivery element includes a polyphosphate ester. Polyphosphate ester is a compound such as that disclosed in U.S. Pat. Nos. 5,176,907; 5,194,581; and 5,656,765 issued to Leong which are incorporated herein by reference in their entirety. Similar to the polyanhydrides, polyphosphate ester is suitable for drug delivery. Unlike the polyanhydrides, the polyphosphate esters have high molecular weights (600,000 MW average), yielding attractive mechanical properties. This high molecular weight leads to transparency, and film and fiber properties. It has also been observed that the phosphorous-carbon-oxygen plasticizing effect, which lowers the glass transition temperature, makes the polymer desirable for fabrication. The highly hydrolytically reactive phosphorous ester bond, the favorable physical properties, and the versatile chemical structure make the polyphosphate esters a superior drug delivery system for a prosthesis. PPE microspheres may also be incorporated into the stent as disclosed in U.S. Pat. No. 5,545,208 to Wolff et al., which is hereby incorporated by reference in its entirety.

The drug-eluting layer may be operably attached to the other layers of the prosthesis, for example, by spray-dipping, coating, annealing, or covalently or noncovalent binding as known in the art.

Non-limiting examples of drugs that may be incorporated into the prosthesis described herein that can be used individually or in different combinations are discussed below.

Paclitaxel, is an antineoplastic compound which is used clinically in commercially available drug-eluting stents. This drug can also be used as an anti-inflammatory agent with an exceptionally narrow therapeutic window beyond which it can be cytotoxic. In some embodiments, the prosthesis may include one drug delivery reservoir with paclitaxel and another drug delivery reservoir with an antineoplastic agent, sometimes in combination with other drugs known for their anti-inflammatory activities (e.g., naproxen) and/or being immunosuppressant (e.g., rapamycin).

Rapamycin is clinically used in commercially available drug-eluting stents. This drug is also used as an immunosuppressant having a wide therapeutic window. However, its use in drug-eluting stents in the prior art may not provide the optimum pharmacokinetics when released from a non-uniform coating. This invention also provides for use of rapamycin in combination with at least one additional bioactive agent, with different pharmacological activity, such as in one or more drug delivery reservoirs. Typical examples of these other agents include endothelial cell growth promoters (e.g., vascular endothelial growth factor or its polypeptide functional analog), smooth muscle growth inhibitors, and antibiotics.

Antineoplastic agents, such as dactimycin, doxorubicin, mitomycin, mitoxantrone, and topotecan, also exhibit antibiotic activities. These can be used individually or in combination with other drugs (that may be loaded in separate drug delivery reservoirs), particularly those known to exhibit anti-inflammatory activity and/or promote endothelial cell growth.

Antineoplastic agents are also folate antagonists, such as methotrexate, The latter drug is also antimetabolite and immunosuppressant but can be an irritant. To mediate the latter effect, methotrexate can be used in combination with an anti-inflammatory drug and/or endothelial cell growth promoters, such as vascular endothelial growth factor (VEGF) or its polypeptide functional analog.

Anti-inflammatory drugs, which can be used alone or in combination with antineoplastic agents and/or immunosuppressants. Examples of these anti-inflammatory drugs include (a) colchicine, which is also an antineoplastic compound that can be used to retard smooth muscle cell proliferation and can preferably be used in combination with an endothelial cell growth promoter, such as VEGF or its polypeptide functional analog; (b) the NSAID, indomethacin; (c) the NSAID, piroxicam, which may also be an immunosuppressant; and (d) the corticosteroid, prednisone, which may also exhibit antineoplastic activity.

Leflunamide, a member of the isoxazole class of drugs, exhibits anti-inflammatory, antiproliferative, and immunosuppressive activities. This can be used alone or in combination with an endothelial cell promoter.

Thalidomide is an anti-inflammatory drug that also exhibits anti-angiogenic and immunosuppressive activities. This can be used alone or in combination with an endothelial cell growth promoter.

Curcumin is an anti-inflammatory drug, which also exhibits antiproliferative activities.

Mycophenolate mofetil is an immunosuppressant that is endowed with anti-inflammatory properties. This can be used alone or in combination with an endothelial cell promoter.

Methotrexate is an anti-inflammatory and immuno-regulatory drug. It exhibits antiproliferative activity and can be used alone or in combination with an endothelial cell growth promoter, such as vascular endothelial growth factor or its polypeptide functional analog.

Dihydrofolate reductase is an anti-infective, antineoplastic, and anti-inflammatory agent. It can be used alone or in combination with an endothelial cell growth promoter.

Deferoxamine has been used extensively as chelation therapy in iron-loaded states and noted recently for its usefulness as an antiproliferative, anti-inflammatory, and immunosuppressive agent. It can be used alone or in combination with an endothelial cell growth promoter.

Antibiotics produced by members of the bacterial genus Streptomyces, such as streptomycin-B, actinomycin-F1, and actinomycin-D, also exhibit antineoplastic and/or immunosuppressive activities.

Antineoplastics which are also antimetabolites, such as fludarabine and fluorouracil, can be used alone or in combination with an anti-inflammatory drug.

Growth factors such as endothelial or fibrous tissue growth factors, agonists or antagonists, or neurotrophic proteins, such as nerve growth factor, can also be incorporated.

In some embodiments, tropomyosin along with troponin could be utilized to regulate the shortening of the muscle protein filaments action and myosin. In resting muscle fibers, tropomyosin is displaced from its normal binding groove by troponin.

In some embodiments regenerative cells such as adult stem cells, vascular endothelial cells, vascular smooth cells including but not limited to myofibril including RNA(MIR) promotes cardiac myofibril gene expression and is important for embryonic heart development. Other similar stem cells such as human embryonic stem cells from Geron (Menlo Park, Calif.) can also be operably attached to one or more layers of the stent.

In some embodiments, the controlled drug release element comprises polyphosphoester microspheres. Layers 200 and 201 of FIG. 1, in some embodiments, can be configured with a certain porosity meeting the Association for the Advancement of Medical Instrumentation (AAMI) standard for vascular graft applications to allow the device to integrate into tissue at the vascular site. This feature would improve lodging within the vessels, as well as promotion of integration and cell growth through the sidewall of the permanent component(s) of the implant to embed the implant in the vascular wall at the treatment site.

FIG. 2A illustrates an embodiment of a prosthesis 108, shown schematically and not to scale, with enlarged, flared end portions 9. The outer drug delivery element and inner tubular membrane are not shown for clarity. The enlarged end portions 9 are created as the ends of fibers 12 from the biodegradable polymer layer (discussed below) running axially across the prosthesis 108 are secured at the distal and proximal end of the prosthesis at 9. As will be discussed, in some embodiments, fibers 12 can be interwoven in an over and under braided configuration intersecting at points such as 14 to form an open mesh or weave construction. The added thickness created by the laminated and/or bonded secured and folded fibers 12 at both ends of the device can be utilized as a platform to create expanded drug delivery reservoirs for one or more drugs at the distal and proximal end of the device, to provide directional drug delivery as well as controlled drug release through surfaces of inner member and/or on the surfaces of the exterior of the outer member (e.g., the drug coating). The fiber ends 9 also provide increased radial support at both ends of the device. The enlarged lateral ends 9 can result in a flared, expanded cross-section 111 as shown in FIG. 2B. When fully deployed, in some embodiments, the inner luminal diameter of the prosthesis is substantially consistent in diameter throughout its length and generally annular shaped, the outer diameter of copolymer layer at the distal and/or proximal end of the device D2 at the expanded state is larger by 0.002 to 0.010 inches, or 0.005 to 0.010 inches in some embodiments larger than the outer diameter at a mid-portion of the device D1, creating one or more drug delivery reservoirs for one or more types of drugs. Alternatively, the drug delivery element may be present not only at the ends but extending partially or completely over the prosthesis.

The stent 108 illustrated in FIG. 2A has in its unconstrained, expanded state a first outer cross-sectional diameter D2 at each end and a second, smaller cross-sectional diameter D1 at the central apex portion of the stent. The cross-sectional diameter of the stent preferably decreases from one end to a central apex portion, and preferably increases from the central apex portion to the second end. The larger cross-sectional diameter D2 at the ends relative to the central apex portion diameter D1 advantageously provides increased radial support for the stent at the first and second ends. In some embodiments, the ratio of D2/D1 is at least about 1.005, 1.01, 1.02, 1.03, 1.04, 1.05, 1.07, 1.10, 1.15, 1.20, 1.25, 1.30, or more.

In some embodiments, the prosthesis is selected to be oversized by at least about 3%, 4%, 5%, 6%, 7%. 8%, 9%, 10%, or more than the diameter of the body lumen that the prosthesis is inserted into, or between about 3% and 10% in some embodiments.

While the prosthesis 108 shown in FIG. 2A has a variable outer diameter, the prosthesis 108 preferably has relatively constant inner diameter throughout its axial length to provide a stable flow path when the prosthesis is placed within a blood vessel.

Figure 2C:
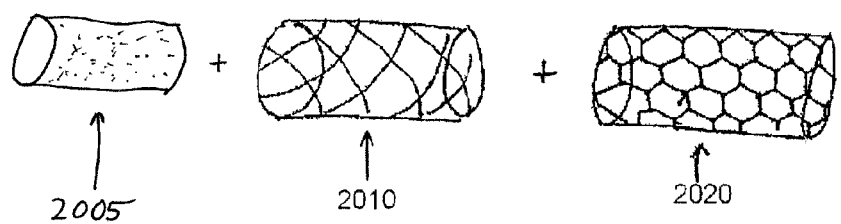
FIG. 2C schematically illustrates a plurality of tubular bodies in which layers 2010 and 2030 can be annealed together to create a stent, according to one embodiment of the invention. Layer 2020 can also be created by spray or dipping coating process.

FIG. 2C illustrates schematically an exploded view of a first tubular body 2005 that may be made of a porous biocompatible material such as ePTFE, PTFE, polyurethane, or similar materials. The second tubular body 2010 comprises a helically wound and or braided polymer that can optionally include a polyphosphoester or other drug coating 2020. A stent may be formed in some embodiments by annealing (e.g., on a mandrel) the first 2005 and second 2010 tubular bodies. The first tubular body 2005 preferably has a smaller diameter than the second tubular body 2010 such that the first tubular body 2005 becomes the inner layer and the second tubular body 2010 becomes the intermediate or outer layer. In some embodiments, a third tubular body 2020 comprising a drug delivery layer may also be present and can be annealed to the second tubular body 2010, or applied on via a coating, spraying or dipping process to form a tri-layer stent.

Biodegradable Layer

The biodegradable intermediate layer may include a biodegradable polymeric material, such as described in U.S. Patent Publication No. 2006/0129222 A1 to Stinson, hereby incorporated by reference in its entirety.

In some embodiments, a blended combination of polymer such as DLPLA-poly(di-lactide) can be utilized. DLPLA is an amorphous polymer exhibiting a random distribution of both isomeric forms of lactic acid, and accordingly is unable to arrange into an organized crystalline structure. This material has lower tensile strength, higher elongation, and a much more rapid degradation time, making it more attractive as a drug delivery system. Poly(1-lactide) is about 37% crystalline, with a melting point of 170-180° C. and a glass-transition temperature of 60-69° C. The degradation time of LPLA is much slower than that of DLPLA, requiring more than 2 years to be completely absorbed. Copolymers of 1-lactide and d1-lactide have been prepared to disrupt the crystallinity of 1-lactide and accelerate the degradation process.

PGA-polyglycolide is the simplest linear aliphatic polyester. PGA was used to develop the first total synthetic absorbable suture, marketed as Dexon in the 1960s by Davis and Geck Inc. (Danbury, Conn.) Glycolide monomer is synthesized from the dimerization of glycolic acid. Ring-opening polymerization yields high-molecular-weight materials, with approximately 1-3% residual monomer present PGA is highly crystalline (45-55%), with a high melting point (220-225° C.) and a glass-transition temperature of 35-40° C. Because of its high degree of crystallization, it is not soluble in most organic solvents; the exceptions are highly fluorinated organics such as hexafluoroisopropanol. Fibers from PGA exhibit high strength and modulus and are too stiff to be used as sutures except in the form of braided material. Sutures of PGA lose about 50% of their strength after 2 weeks and 100% at 4 weeks, and are completely absorbed in 4-6 months. Glycolide has been copolymerized with other monomers to reduce the stiffness of the resulting fibers.

Lactide is the cyclic dimer of lactic acid that exists as two optical isomers, d and 1. 1-lactide is the naturally occurring isomer, and d1-lactide is the synthetic blend of d-lactide and 1-lactide. The homopolymer of 1-lactide (LPLA) is a semi crystalline polymer. These types of materials exhibit high tensile strength and low elongation, and consequently have a high modulus that makes them more suitable for load-bearing applications such as in orthopedic fixation and sutures. Poly (d1-lactide) (DLPLA) is an amorphous polymer exhibiting a random distribution of both isomeric forms of lactic acid, and accordingly is unable to arrange into an organized crystalline structure. This material has lower tensile strength, higher elongation, and a much more rapid degradation time, making it more attractive as a drug delivery system. Poly(1-lactide) is about 37% crystalline, with a melting point of 175-178° C. and a glass-transition temperature of 60-65° C. The degradation time of LPLA is much slower than that of DLPLA, requiring more than 2 years to be completely absorbed. Copolymers of 1-lactide and d1-lactide have been prepared to disrupt the crystalline of 1-lactide and accelerate the degradation process.

Mechanical properties generally increase with increasing molecular weight. For instance, the strength and modulus of PLA generally increases with increasing molecular weight. Degradation time generally decreases with decreasing initial molecular weight (i.e., a stent made of a low molecular weight polymer would be bioabsorbed before a stent made of a high molecular weight polymer). Low molecular weight PLA is generally more susceptible to thermo-oxidative degradation than high molecular weight grades, so an optimum molecular weight range should be selected to balance properties, degradation time, and stability. The molecular weight and mechanical properties of the material generally decreases as degradation progresses. PLA generally has a degradation time greater than 1 year. PLA has a glass transition temperature of about 60° C., so care must be taken not to store products in environments where high temperature exposure may result in dimensional distortion.

PLA, PLLA, PDLA and PGA include tensile strengths of from about 40 thousands of pounds per square inch (psi) to about 120 psi; a tensile strength of 80 psi is typical; and a preferred tensile strength of from about 60 psi to about 120 psi. Polydioxanone, polycaprolactone, and polygluconate include tensile strengths of from about 15 psi to about 60 psi; a tensile strength of 35 psi is typical; and a preferred tensile strength of from about 25 psi to about 45 psi.

PLA, PLLA, PDLA and PGA include tensile modulus of from about 400,000 pounds per square inch (psi) to about 2,000,000 psi; a tensile modulus of 900,000 psi is typical; and a preferred tensile modulus of from about 700,000 psi to about 1,200,000 psi. Polydioxanone, polycaprolactone, and polygluconate include tensile modulus of from about 200,000 psi to about 700,000 psi; a tensile modulus of 450,000 psi is typical; and a preferred tensile modulus of from about 350,000 psi to about 550,000 psi.

PLLA filament has a much lower tensile strength and tensile modulus than, for example, Elgiloy metal alloy wire which may be used to make braided stents. The tensile strength of PLLA is about 22% of the tensile strength of Elgiloy. The tensile modulus of PLLA is about 3% of the tensile modulus of Elgiloy. Stent mechanical properties and self-expansion are directly proportional to tensile modulus of the material. As a result, a PLLA filament braided stent made to the same design as the metal stent has low mechanical properties and would not be functional. The invention advantageously provides polymeric braided stents with radial strength similar to metal stents and the required mechanical properties capable of bracing open endoluminal strictures.

A bioabsorbable PLLA braided tubular stent changes size when constrained onto a catheter delivery system and when deployed. A deployed PLLA stent is generally longer in length and smaller in diameter than a PLLA stent prior to loading. For example, PLLA stents that were initially 30 mm long with external diameters of about 10.7 mm had deployed lengths of about 90 mm with diameters of about 6.3 mm.

Self-expanding stents can be formed from a number of resilient filaments which are helically wound and interwoven in a braided configuration. The stents assume a substantially tubular form in their unloaded or expanded state when they are not subjected to external forces. When subjected to inwardly directed radial forces the stents are forced into a reduced-radius and extended-length loaded or compressed state. The stents are generally characterized by a longitudinal shortening upon radial expansion.

In one preferred embodiment, the device is a stent which includes a plurality of elongate polylactide bioabsorbable polymer filaments, helically wound and interwoven in a braided configuration to form a tube. Bioabsorbable implantable endoprostheses such as stents, stent-grafts, grafts, filters, occlusive devices, and valves may be made of poly(alpha-hydroxy acid) such as poly-L-lactide (PLLA); poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(amino-acids), or related copolymers materials, each of which have a characteristic degradation rate in the body. For example, PGA and polydioxanone are relatively fast-bioabsorbing materials (weeks to months) and PLA and polycaprolactone are a relatively slow-bioabsorbing material (months to years).

A stent constructed of a bioabsorbable polymer provides certain advantages relative to metal stents such as natural decomposition into non-toxic chemical species over a period of time. Also, bioabsorbable polymeric stents may be manufactured at relatively low manufacturing costs since vacuum heat treatment and chemical cleaning commonly used in metal stent manufacturing are not required.

In comparison, a metal self-expanding stent generally has about the same dimensions before loading and after deployment. For metal stents, if it is known that the patient has a 9 mm diameter vessel, then a 10 mm metal stent (stent is intentionally oversized by about 1 mm) is loaded onto the delivery system for implantation. This rule is not applicable for a polymer stent because more oversizing is necessary.

PLLA-Poly(L-lactic acid) fibers are processed by a two step melt-spinning method (extrusion and hot draw) from PLLA with three different Viscosities -average molecular weight of approximately (494000 g/mol, 305000 g/mol, and 262000 gmol). Before spinning, the polymer flakes are first milled into powders and dried under vacuum. The extrusion die is operated at a temperature of 230° C.±30° C. In some embodiments, depending on the diameter of fiber utilized, up to 38-spindle braiders/winders may be required for manufacturing.

The outer layer surface structure can vary from particle beads texture for enhanced lodging to fibrous materials. The fiber manufacturing process includes a melt extrusion immediately followed by a drawing process to create self-reinforced embodiment. To attain maximum radial strength for the device the drawing of the molten referenced materials can occur, e.g., at angle ranging from 60° to 140° degrees. The isotropic polymer is transformed into highly anisotropic self-reinforced configuration. The self-reinforced fiber has a high degree of molecular orientation in the direction of the long axis of the fiber. The vacuum dried material is extruded by an industrial grade extruder having a 1.0 mm monofilament die. In the drawing process, the materials are oriented with draw ratios of approximate 6.0, corresponding to final diameter of 0.029 mm. The self reinforced fibers are braided into a cylindrical/tubular shape onto a 4-11 mm mandrel using two vertically operating 24-spindle braiding/winding machines. Heat treatment takes place in the vacuum oven at 120-160° C. for 7-25 minutes. Next the stents are left in at room temperature for approximately 15 to 25 minutes. The viscosity-average molecular weight, in some embodiments, can be approximately 220,000 g/mol after extrusion. The drawing processes decrease the viscosity average weight to about 48,000 g/mol.

The mandrel's outer diameter, which may be from about 4 mm to about 11 mm depending on the desired clinical application, can be larger than the outer diameter of the prosthesis by a factor of 15% to 25% to attain the final diameter post heat treating. In one embodiment, a 10 mm in diameter device would be fabricated/heat treated on a 12 mm OD mandrel.

The biodegradable polymer is preferably interwound radially to an inner membranous layer, and can be annealed together, in some embodiments, at temperatures ranging from 300 to 500 degrees Fahrenheit.

The biodegradable filament layer 201 can also be annealed on a mandrel or otherwise attached to the inner layer 200, as illustrated schematically in FIG. 1. Shown first is a first tubular body 200 then a helically wound and braided polymer body 201. The multi-layered stent may be formed in some embodiments by annealing layers 200 and 201. The first tubular body 200 preferably has a smaller diameter than the second tubular body 201 such that the first tubular body 200 becomes the inner layer and the second tubular body 201 becomes the outer layer. One or more drug release layers 202 may be present on one or more surfaces of layers 200 and/or 201 as previously noted.

The prosthesis is preferably configured to be at least partially bioresorbable and can in some embodiments, degrade in vivo over 1-3 years. Heavy molecular weight polymers possess higher tensile strength and would require additional time to intergrade to the vascular site.

Figure 3:
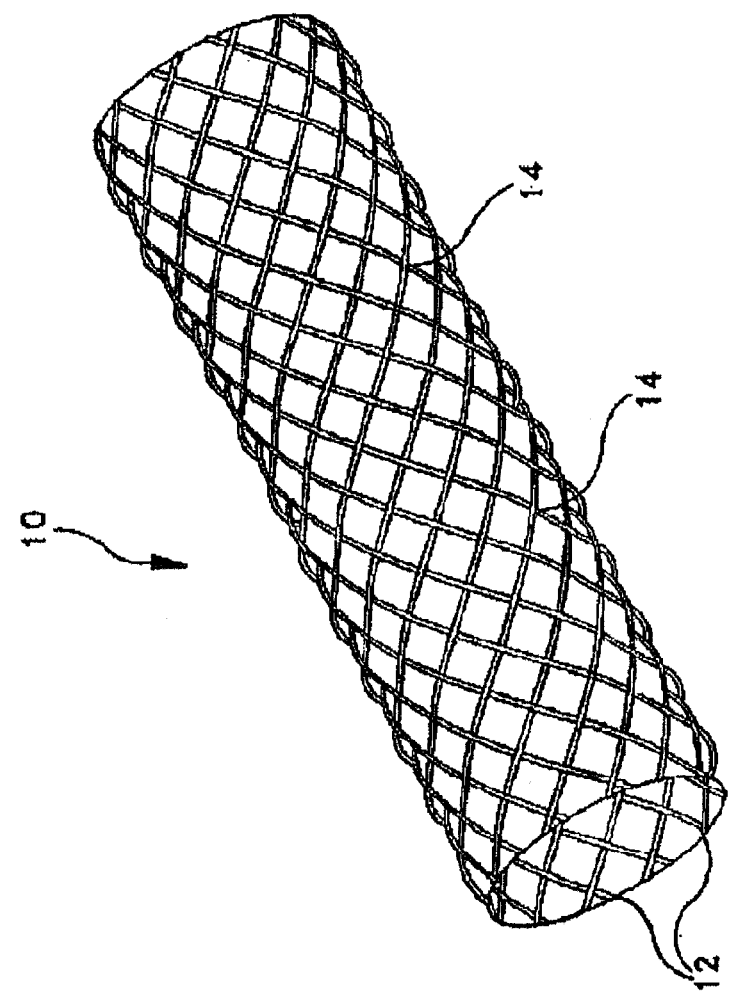

One embodiment of a bioabsorbable polymeric layer 10 is illustrated generally in FIGS. 3 and 4. Biodegradable stent layer 10 is generally tubular and formed from two sets of oppositely-directed, parallel, spaced-apart and helically wound elongated strands or filaments 12. The sets of filaments 12 are interwoven in an over and under braided configuration intersecting at points such as 14 to form an open mesh or weave construction. As described in greater detail below, at least one and preferably all filaments 12 are made of one or more commercially available grades of polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester; poly(amino acids), poly(alpha-hydroxy acid) or related copolymers materials. Methods for fabricating stents 10 are generally known and disclosed, for example, in U.S. Pat. No. 4,655,771 to Wallsten and U.S. Pat. No. 5,061,275 to Wallsten et al., hereby incorporated by reference in their entirety.

Stent layer 10 is shown in its expanded or relaxed state in FIGS. 3 and 4, i.e., in the configuration it assumes when subject to no external loads or stresses. The filaments 12 are resilient, permitting the radial compression of stent layer 10 into a reduced-radius, extended-length configuration or state suitable for delivery to the desired placement or treatment site through a body vessel (i.e., transluminally). Stent layer 10 is also self-expandable from the compressed state, and axially flexible.

Stated another way, stent layer 10 is a radially and axially flexible tubular body having a predetermined diameter that is variable under axial movement of the ends of the body relative to each other. The stent layer 10 is composed of a plurality of individually rigid but flexible and elastic thread elements or filaments 12, each of which extends in a helix configuration along a longitudinal center line of the body as a common axis. The filaments 12 define a radially self-expanding body. The body may be provided by a first number of filaments 12 having a common direction of winding but axially displaced relative to each other, and crossing a second number of filaments 12 also axially displaced relative to each other but having an opposite direction of winding.

The tubular and self-expandable body or structure formed by the interwoven filaments 12 is a primary prosthetically-functional structure of stent layer 10. However, it is known that other structures and features can be included in stents, and in particular features which enhance or cooperate with the tubular and self-expandable structure or which facilitate the implantation of the structure. One example is the inclusion of radiopaque markers on the structure which are used to visualize the position of the stent through fluoroscopy during implantation. Another example is the inclusion of a covering 15 or additional interwoven filaments, for instance, to reduce the porosity or open spaces in the structure so that the stent can be used to prevent tissue in-growth or be used as a graft. Other examples include collapsing threads or other structures to facilitate repositioning and removal of the stent. Furthermore, many of the desirable features and properties of stent layer 10 will be present if some, but not all, of the filaments 12 are made of a bioabsorbable polymeric material.

An implantable bioabsorbable stent layer 10 may be made by a preferred method of braiding such that 10-36 independent strands of 0.15-0.60 mm diameter bioabsorbable polymeric filament are interwoven into helical shape strands on a round bar mandrel of 3-30 mm diameter such that one-half of the number of helical strands are wound clockwise and one-half are wound counterclockwise and such that each clockwise helical strand is adjacent (interbraided) to a counterclockwise strand, the tubular braid is made with strand braid angles (angle between two filaments in the longitudinal or axial direction) of 120-150 degrees (pitch angles, i.e., the angle between a filament and transverse axis of the stent that may be between about 15-45 degrees) while on the braid bar mandrel, the braid is slid off of the braid bar and onto a 0.2-10 mm smaller diameter annealing bar or tube mandrel, each end of the braid pulled or compressed to cause axial extension or compression of the braid on the anneal mandrel, or left free, and each end of the braid secured on each end of the anneal mandrel to fix the preset axial position of the braid, or left free, annealing the braid on the anneal mandrel at a temperature between the glass-transition temperature and melting temperature of the polymer for 5-120 minutes in air, vacuum, or inert atmosphere, cooling the annealed braid on the anneal mandrel to about room temperature, sliding the braid off of the anneal mandrel and cutting it to the desired stent length. Another preferred embodiment includes at least one bioabsorbable-radiopaque marker strand.

FIG. 5 is a cross-sectional view of one of the polymeric filaments 12. As shown, the filaments 12 may be substantially circular in cross section, although other configurations such as oral or rectangular (ribbon) may be used.

In some embodiments, the polymeric filament intermediate layer described above can be operably attached, such as radially interwound to a biocompatible inner tubular membrane layer. The membrane is preferably a synthetic material such as, for example, a thermoplastic such as ePTFE, Teflon, polyethylene, or polyurethane. In some embodiments, the membrane and the polymeric filaments may be annealed together, such as, for example, at a temperature ranging from about 300° F. to about 500° F. This layer can be the inner lumen layer, although it could also be an outer layer, or both an inner and outer layer to promote cellular in-growth.

In some embodiments, a lumen layer, such as an inner layer includes a porous media feature network of open-celled directional pores for enhanced fluid dynamics. In some embodiments, the pore size may be constant throughout the membranous layer. The prosthesis may also be prepared with different mean pore sizes. Pore size can be an important parameter in that certain macromolecular drugs may be excluded from use where the pore size is very small. The pore size may also play a role in determining the extent of cellular infiltration or tissue in-growth during implantation of the stent. While cellular in-growth is sometimes desirable, it can also lead to complications such as infection and difficulty in removing the stent. Stents with a mean pore size of greater than about 10 microns can allow infiltration of cellular sized biomaterials; stents with mean pore sizes in the range of 1-10 microns may accommodate infiltration of some of the above bio-materials. Stents with pore sizes less than about 1 micron will not generally accommodate infiltration of any of the above biomaterials but can accommodate infiltration of macromolecular and small biomaterials. Thus, the pore size of the stent may be varied to foster or inhibit cellular infiltration and/or tissue in-growth. Of course, the pore size may also be varied to facilitate delivery of drugs of different molecular sizes.

Optionally present in one or more of the layers are radiopaque marker elements to improve visualization of the stent, for example, under fluoroscopy. Also the delivery system/catheter may possess radiopaque markers defining the distal and proximal end of the vascular prosthesis (stent like device) while in the delivery system. The flexible nature and reduced radius of the compressed prosthesis enables it to be delivered through relatively small and curved vessels in percutaneous transluminal angioplasty. In some embodiments, the marker elements can either be located directly adjacent the ends of the stent in a manner only slightly increasing a length of the stent or the marker elements can be spaced from the adjacent portions of the stent in a manner causing the marker elements to enhance somewhat the overall length of the stent. With the radiopaque marker elements in place attached to the ends of the stent, the location and orientation of the stent can be precisely determined both before, during, and after implantation and radial expansion of the stent within the body lumen.

Figure 6:
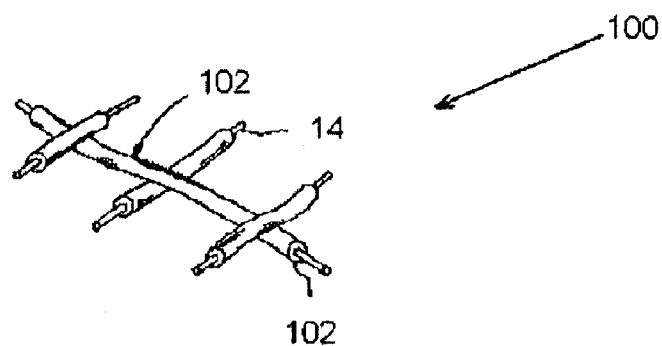
FIG. 6 illustrates a schematic cut-away view of a woven filament layer with a coated drug-release layer, according to one embodiment of the invention.

FIG. 6 illustrates a schematic cut-away view of a portion of the wall of a stent 100 that may be as in FIG. 1 with an inner layer comprising a plurality of bioabsorbable polymer filaments 14. In some embodiments, the filaments 14 are radially interwound with ePTFE, nylon, polypropylene, or another biocompatible material. The stent 100 also comprises an outer layer 102 with a controlled drug release element, such as, for example, polyphosphoester microspheres. The outer layer 102 may be, in some embodiments, spray-dipped, coated, annealed, bound covalently or noncovalently to the inner layer. Thus, the outer layer may be a tubular layer as illustrated in FIGS. 1 and 2c or it may be a layer of coating surrounding a portion or all of the individual fibers in the intermediate woven layer as shown in FIG. 6.

Figure 7:
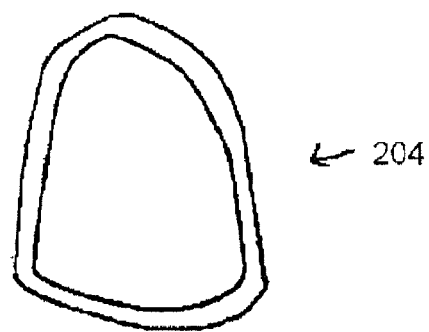
FIG. 7 illustrates a stent with a non-circular acorn-shaped cross-section, according to one embodiment of the invention.

FIG. 7 illustrates schematically a cross-section through a stent, according to one embodiment of the invention. The cross-sectional shape 204 of the stent may be non-circular, and may be acorn-shaped as shown. While the device is inserted/loaded in the delivery system, the constructed embodiment tends to take a set shape, this condition directly relates to the delivery system OD size, and the stent folding methods in the delivery system/catheter as described below. Once the sheath of the delivery system/catheter is pulled back in a proximal direction and the device is released at the target site the device then transforms into a round and circular shape through flow through the inner lumen. Initially it may create a better lodging condition once the device has intergraded in the vascular site it would contour to the specific shape of the body lumen.

Figures 8, 9, 10, 11:
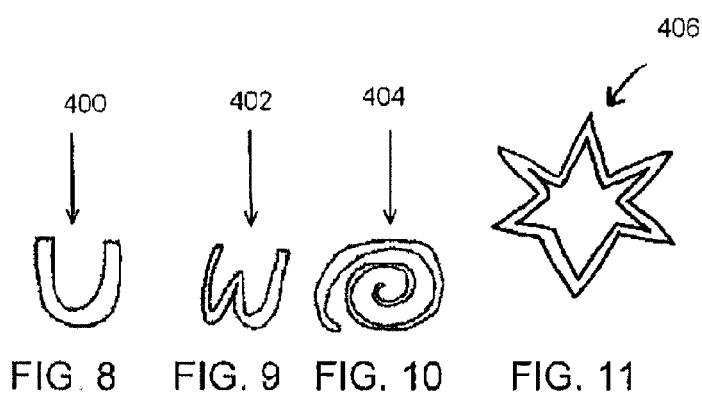
FIGS. 8-11 illustrate various folded stent configurations, according to some embodiments of the invention.

FIGS. 8-11 illustrates several non-limiting examples of the self-expandable stent in a compressed configuration. The compressed shape may be, for example, U-shaped 400 as shown in FIG. 8, W-shaped 402 as shown in FIG. 9, "carpet rolled" 404 as shown in FIG. 10, or "starburst" radially compressed shape 406 as shown in FIG. 11. One of ordinary skill in the art will appreciate that many other compressed prosthesis configurations are possible that do not necessarily have to be compressed radially inwardly.

The prosthesis of the present invention can be implanted in various locations. In addition to the large coronary vessels such as the left main, circumflex, left anterior descending, or right coronary artery, the stent may advantageously be placed in the smaller branches of the coronary arteries, such as the diagonals or posterior descending artery, or various peripheral vessels such as the femoral, carotid, or Circle of Willis cerebral vessels. The stent is also particularly advantageous for curved and tortuous vessels, some of which are mentioned above. The specific features includes but not limited to self expanding design, diameters and length specifications, and drug delivery reservoirs. The prosthesis may also be placed in veins and non-vascular lumens such as the biliary tree, esophagus, intestines, ureter, urethra, trachea, bronchi, and the like.

In some embodiments, a peripheral (non-coronary) stent may have a length of between 5-20 cm, a wall thickness of 0.009 of an inch to 0.015 of an inch, a compressed outside diameter of 7 French to 15 French and an unfolded outside diameter of 4 cm to 11 cm. For coronary applications, the end device may possess the following parameters in certain embodiments: 2-5 mm outer diameter; 10-40 mm length; 0.004-0.007 inch wall thickness.

FIGS. 12-19 illustrate various delivery devices and methods that may be used with the prosthesis shown.

Figure 12:
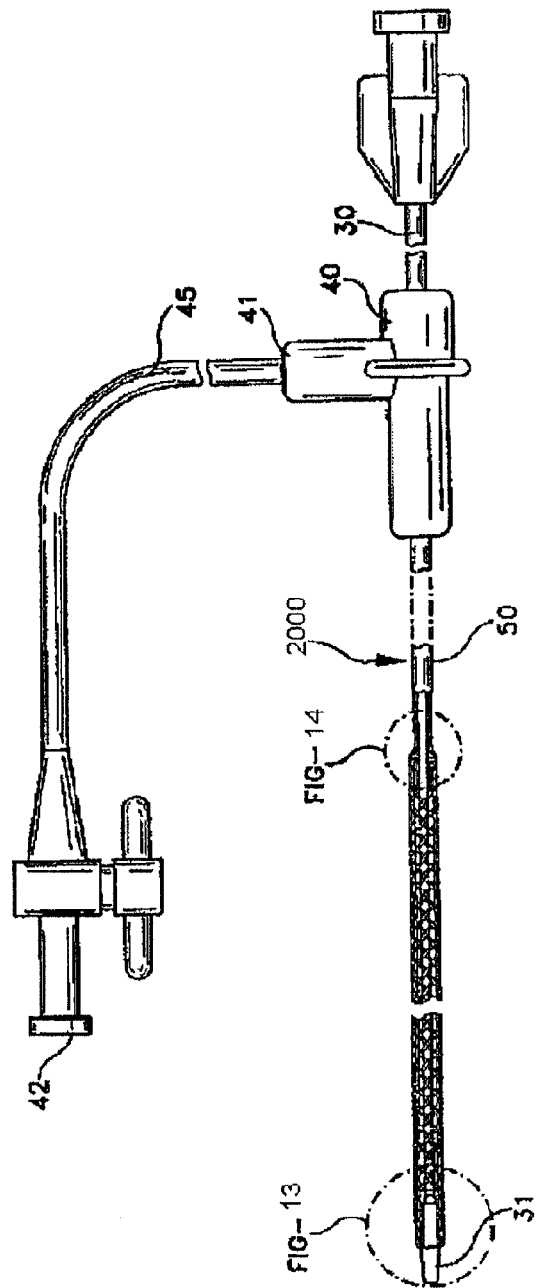
FIGS. 12-20 illustrate various devices for delivery of a stent to a body lumen, according to some embodiments of the invention.
Figure 13:
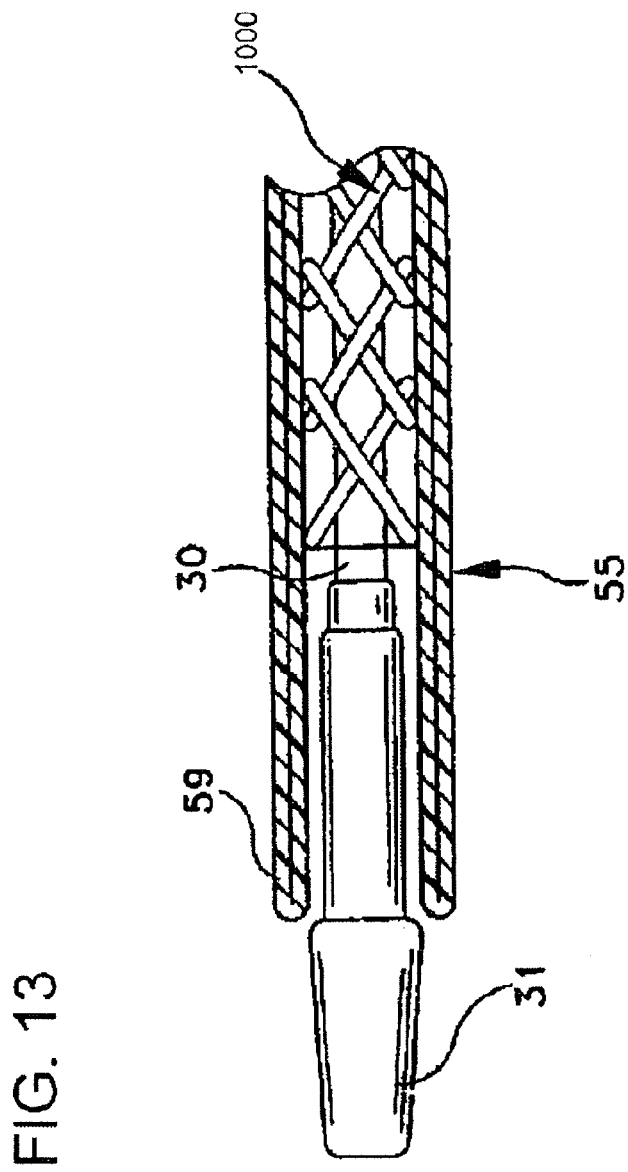
Figure 14:
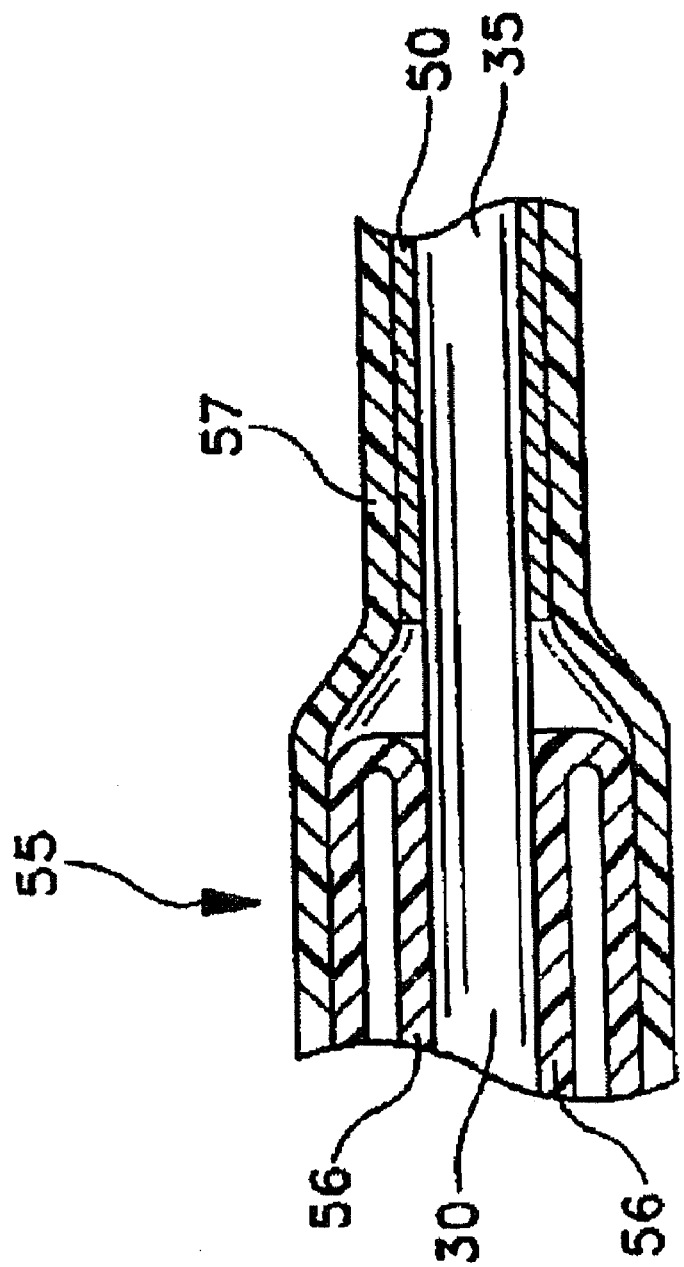
Figure 15:
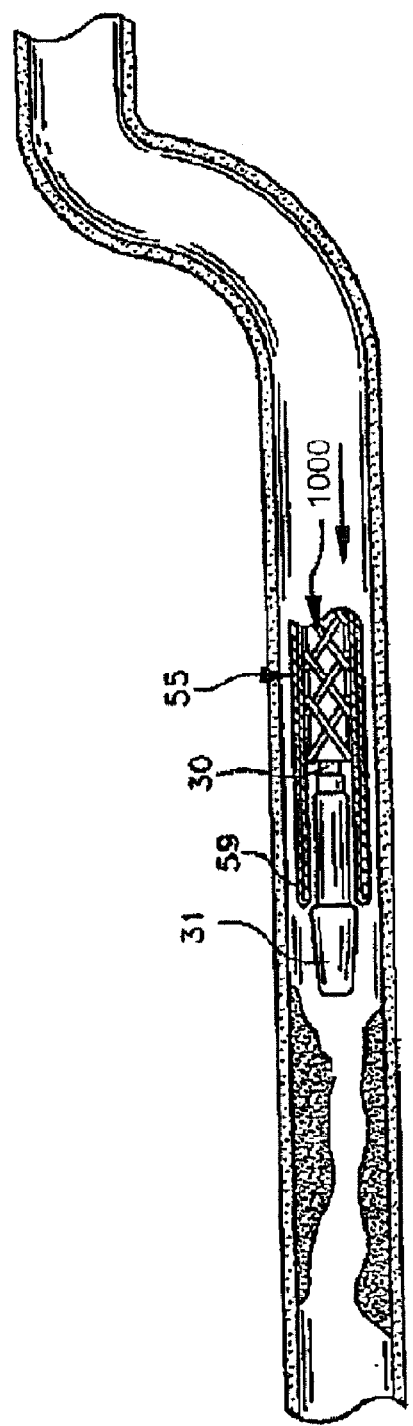
Figure 16:
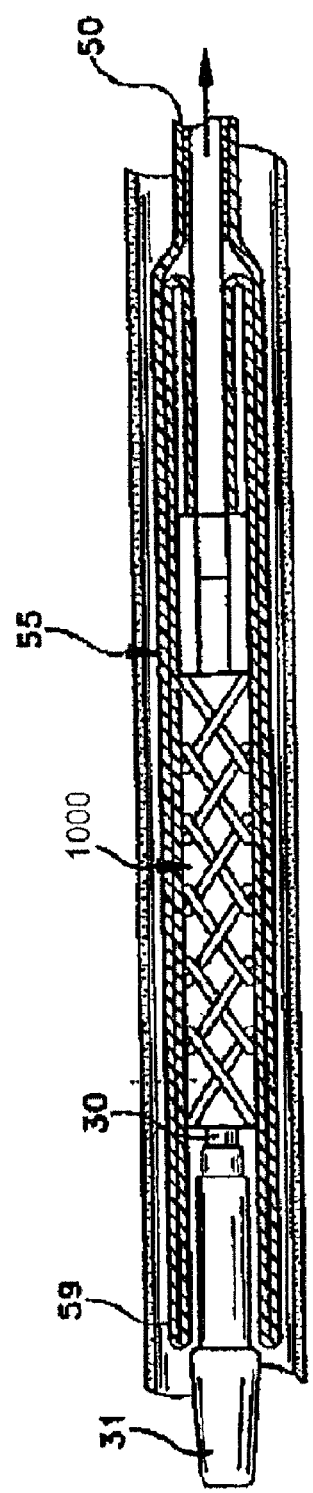
Figure 17:
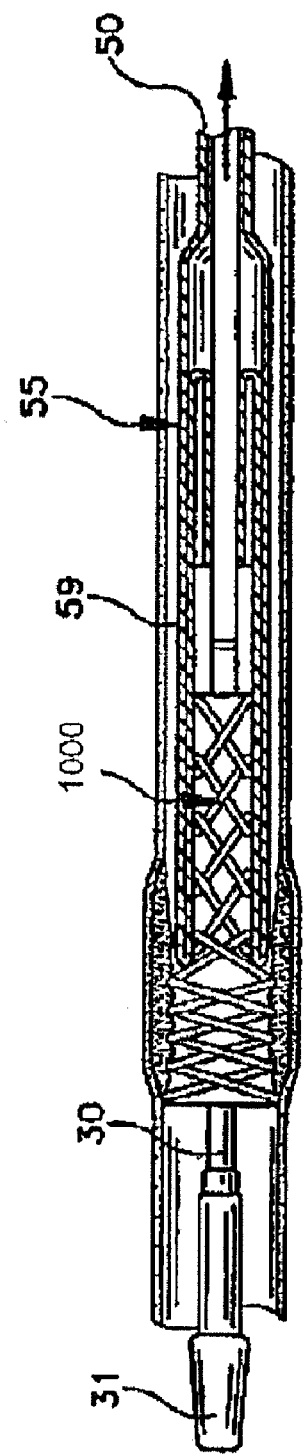
Figure 18:
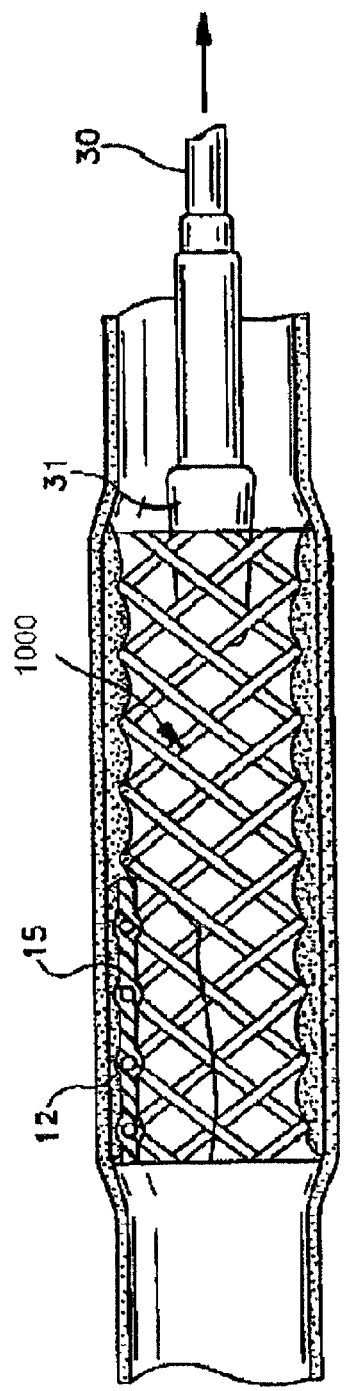

FIGS. 12-14 are illustrations of a coaxial inner/outer tube catheter delivery device 2000 for delivering a stent 1000 to a treatment site in a body vessel. An extension 45 extends from side port 41 to an opening 42.

As shown, stent 1000 may be carried by the distal portion of delivery device 20, and is placed on the delivery device in a radially contracted or compressed state, such as, for example, illustrated in FIGS. 8-11. The proximal portion of delivery device 2000 generally remains outside of the body for manipulation by the operator.

The manner by which delivery device 2000 is operated to deliver stent 1000 to a treatment site in a body vessel or lumen including curved sections is illustrated in FIGS. 15-18. As shown, stent 1000 is placed in a radially compressed state in a surrounding relationship to the outer distal end of inner tube 30. A tip 31 is disposed at the distal end of tube 30. Stent 1000 is constrained on inner tube 30 by the double-walled section of coaxially designed delivery system 55. It is important that stent 1000 not be confined too tightly on inner tube 30. Coaxially designed delivery system 55 should apply just enough force to stent 1000 to hold stent 1000 in place. The double-walled section of coaxially designed delivery system 55 can be removed from around stent 1000 by pulling valve body 40 (see FIG. 12) and proximal tube 50 in a proximal direction. The double-walled section "rolls" off stent 1000. No sliding movements take place between stent 1000 and inner wall 56 (FIG. 14) which contacts stent 1000. Opening 59 are located in the double wall section of the opening 55. Along with the movement of the double-walled section in a proximal direction, the distal end of stent 1000 will be exposed in a radial direction to engagement against the wall of the body vessel. As the double-walled section of the outer member of the coaxially designed delivery system 55 continues moving proximally, more of stent 1000 expands in a radial direction until the entire length of stent 1000 is exposed and engages the wall of a body vessel.

Lumen 35 (FIG. 14) is used to enable delivery device 2000 (FIG. 12) to follow a guide wire (not shown) previously inserted percutaneously into the body vessel. The lumen of inner tube 30 can also be used to introduce a contrast fluid to the area around the distal end of delivery device 2000 so the position of delivery device 2000 can be detected (e.g., through the use of fluoroscopy or X-ray techniques).

The stents of the present invention may be delivered by alternative methods or using alternative devices. For instance, the device described in Heyn et al. U.S. Pat. No. 5,201,757 may be utilized, which is incorporated by reference in its entirety herein.

Figure 19:
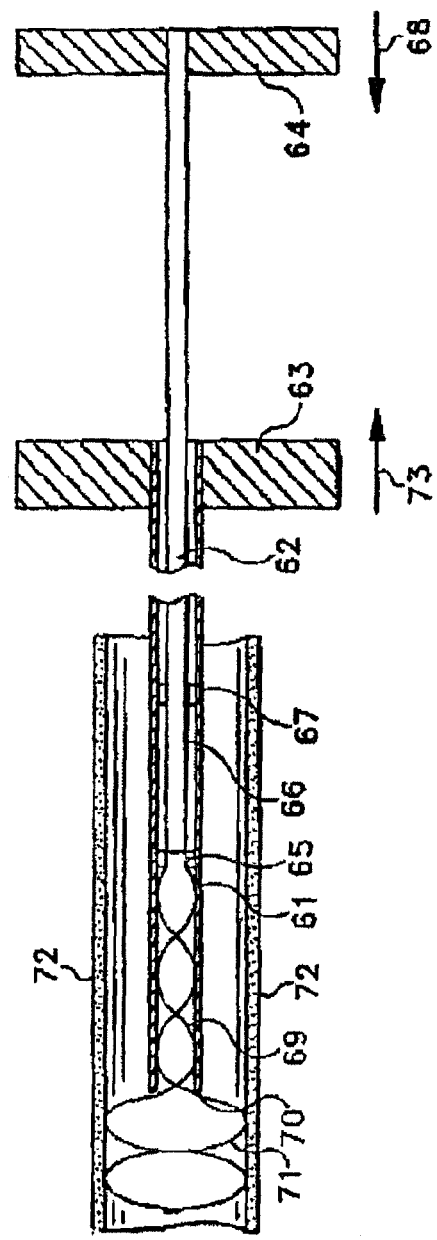

FIG. 19 illustrates a delivery device with an outer tube 61 including member 63 and an inner tube 62 including members 64, 65. Stent 1000 may be inserted in a collapsed state in region 66, and one position of member 65 is shown at about region 67. Member 64 may move in the direction of arrow 68 to push the stent out through end 70 into contact with the interior of wall 72. The stent 1000 is shown as lines 69, 71. The end 70 may be moved by moving member 63 in the direction of arrow 73.

Figure 20:
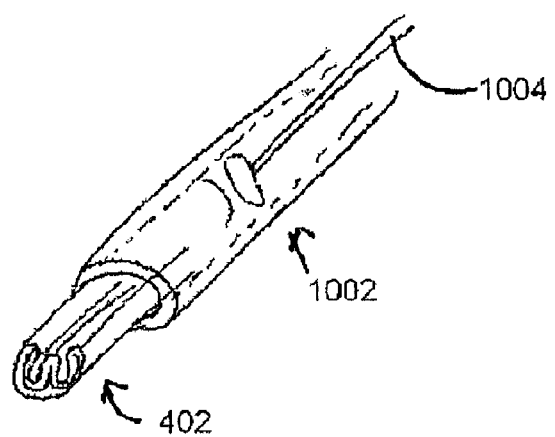

FIG. 20 is a schematic angled perspective view of a stent 402 folded into a "W"-like shape within a delivery catheter 1002. Pusher element 1004 may be used to deploy stent 402 into a desired location in the body lumen, where it can assume its expanded configuration. As described above, the stent 402 with enlarged lateral ends may reduce the risk of undesirable stent migration.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A biodegradable prosthesis, comprising:
    a first end, a second end, and an elongate tubular body with a lumen therethrough;
    a first layer comprising a first bioactive agent;
    a second layer comprising a set of flexible interbraided bioabsorbable filaments; and
    a third layer comprising a porous thermoplastic material,
    wherein the prosthesis has a first cross-sectional outer diameter at the first end, a second cross-sectional outer diameter at the second end, and a third cross-sectional outer diameter at a mid-point on the prosthesis axially displaced from the first end and the second end of the prosthesis, wherein the prosthesis is configured such that the first end and the second end both comprise a first wall, wherein a portion of the first wall is folded over to form a second wall, wherein the second wall is secured to the first wall to provide enhanced radial support such that the first cross-sectional outer diameter and the second cross-sectional outer diameter are both larger than the third cross-sectional outer diameter while the prosthesis is in a first, radially compressed configuration for delivery as well as when the prosthesis is in a second, radially enlarged configuration within a blood vessel, wherein the prosthesis has a continuous, cylindrical cross-sectional inner diameter throughout its axial length to provide a stable flow path when the prosthesis is placed within the blood vessel, wherein the prosthesis comprises a drug delivery reservoir between the first wall and the second wall, wherein the drug delivery reservoir comprises a second bioactive agent.

2. The prosthesis of claim 1, wherein the second layer is radially interwound to the third layer.

3. The prosthesis of claim 1, wherein the porous thermoplastic material comprises ePTFE.

4. The prosthesis of claim 1, wherein the first cross-sectional outer diameter at the first end of the prosthesis is at least 0.005 inches larger than the third cross-sectional outer diameter.

5. The prosthesis of claim 1, wherein the first cross-sectional outer diameter at the first end of the prosthesis is between about 5-9% greater than the third cross-sectional outer diameter.

6. The prosthesis of claim 1, wherein the first bioactive agent comprises a drug.

7. The prosthesis of claim 6, wherein drug is selected from the group consisting of: paclitaxel, rapamycin, zotarolimus, and tacrolimus.

8. The prosthesis of claim 1, wherein the second layer is annealed to the third layer.

9. The prosthesis of claim 1, wherein the bioabsorbable filaments comprise at least one material selected from the group consisting of: polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester; poly(amino acids), and poly(alpha-hydroxy acid).

10. The prosthesis of claim 1, further comprising at least one radioopaque marker element.

11. The prosthesis of claim 1, further comprising a second drug delivery element on an inner surface of the first layer of the prosthesis.

12. A medical system comprising a catheter and a radially expandable prosthesis as in claim 1, carried by a distal section of the catheter.

13. A system as in claim 12, further comprising a lubricious coating on the catheter.

14. The prosthesis of claim 1, configured to provide structural integrity to a body lumen for no more than about two years.

15. The prosthesis of claim 1, wherein the first layer is coated with a first drug for treating a diseased lumen, and the surface of the third layer is provided with a second drug, for elution into the blood flow.

16. The prosthesis of claim 1, wherein the third layer is configured to remain in the vascular lumen permanently and will permit cell growth therethrough.

17. The prosthesis of claim 1, wherein the third layer is the outermost layer.

18. The prosthesis of claim, wherein the third layer is the innermost layer.

19. The prosthesis of claim 1, wherein the first bioactive agent comprises a stem cell.

20. The prosthesis of claim 1, wherein the second wall is bonded to the first wall.

* * * * *

UNITED STATES PATENT AND TRADEMARK OFFICE
CERTIFICATE OF CORRECTION

| | | |
|---|---|---|
| PATENT NO. | : 8,303,650 B2 | Page 1 of 1 |
| APPLICATION NO. | : 11/972406 | |
| DATED | : November 6, 2012 | |
| INVENTOR(S) | : Shokoohi | |

It is certified that error appears in the above-identified patent and that said Letters Patent is hereby corrected as shown below:

In the Specification

In column 7 at line 62, Change "methotrexate," to --methotrexate.--.

In the Claims

In column 18 at line 53, In Claim 18, change "claim," to --claim 1,--.

Signed and Sealed this
Twenty-fifth Day of November, 2014

Michelle K. Lee
*Deputy Director of the United States Patent and Trademark Office*